Figure 1:
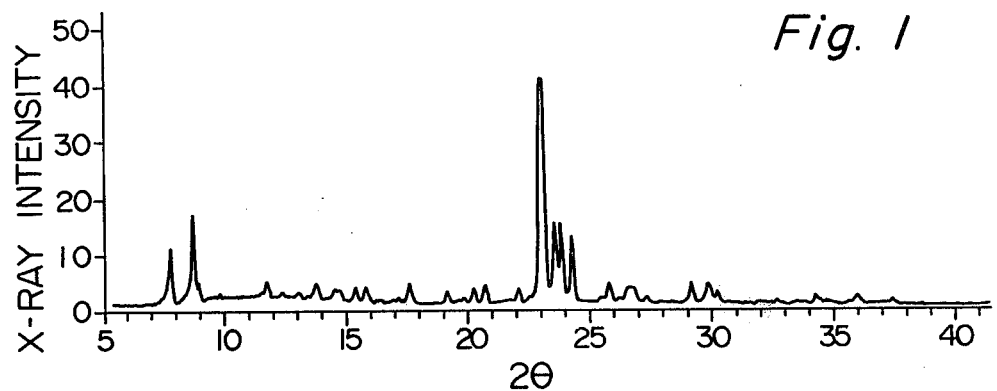

United States Patent [19]

Suzuki et al.

[11] 4,444,738

[45] Apr. 24, 1984

[54] PROCESS FOR PRODUCING CRYSTALLINE ALUMINOSILICATES

[75] Inventors: Takashi Suzuki; Shoichiro Hashimoto; Rieko Nakano, all of Niigata, Japan

[73] Assignee: Mitsubishi Gas Chemical Company, Inc., Japan

[21] Appl. No.: 323,989

[22] Filed: Nov. 23, 1981

[30] Foreign Application Priority Data

Dec. 3, 1980 [JP] Japan ................... 55-170649

[51] Int. Cl.³ ............................................ C01B 33/28
[52] U.S. Cl. ................................. 423/329; 423/328; 502/69; 502/77
[58] Field of Search ............ 423/329, 328, 118, 328 T; 252/455 Z; 502/69, 77

[56] References Cited

U.S. PATENT DOCUMENTS

| | | | |
|---|---|---|---|
| 3,702,886 | 11/1972 | Argauer et al. | 423/328 |
| 3,839,539 | 10/1974 | Elliott | 423/329 |
| 3,939,246 | 2/1976 | Rollmann | 423/118 |
| 3,941,871 | 3/1976 | Dwyer et al. | 423/326 |
| 4,025,571 | 5/1977 | Lago | 423/328 |
| 4,088,605 | 5/1978 | Rollmann | 423/328 |

OTHER PUBLICATIONS

R. Von Ballmoos et al., "Zoned Aluminium Distribution in Synthetic Zeolite ZSM-5".

Primary Examiner—Edward J. Meros
Assistant Examiner—Steven Capella
Attorney, Agent, or Firm—Wenderoth, Lind & Ponack

[57] ABSTRACT

A process for producing a crystalline aluminosilicate which comprises hydrothermally reacting a starting mixture composed of a silicon compound, an aluminum compound, an alkali metal compound, a compound capable of releasing an organic cation in water, and water, characterized in that said starting mixture comprises at least two colloids having different silicon/aluminum atomic ratios, and that the hydrothermal reaction is carried out, as required, in the presence of a fluorine compound.

14 Claims, 6 Drawing Figures

PROCESS FOR PRODUCING CRYSTALLINE ALUMINOSILICATES

This invention relates to a process for producing crystalline aluminosilicates. More specifically, it pertains to a process for producing crystalline aluminosilicates which exhibit very good properties as adsorbents or catalysts.

Known crystalline aluminosilicates include naturally occurring aluminosilicates and synthetic zeolites hydrothermally synthesized from an aqueous solution containing silicon and aluminum.

In recent years, synthetic zeolites having a different skeletal structure from naturally occurring zeolites, such as ZSM-5 (see Japanese Patent Publication No. 10064/1971) and ZSM-34 (Japanese Laid-Open Patent Publication No. 58499/1978), have been hydrothermally synthesized in the presence of quaternary ammonium compounds. Particularly, ZSM-5 crystallized in the presence of a tetrapropyl ammonium compound is a unique zeolite which gives a crystalline phase over a wide $SiO_2/Al_2O_3$ mole ratio in the skeleton. These crystalline aluminosilicates have found wide applications as adsorbents or catalysts of high performance because they are porous and show selectivity with regard to shapes of molecular units. For example, they are used as dehydrating agents for organic matter or as isomerization catalysts for hydrocarbons.

Crystalline aluminosilicate catalysts, like general solid catalysts, are required to have high activity, good selectivity and long active lifetimes. Not only the type of the crystalline aluminosilicate and the type of the skeletal structure, but also the particle size and shape of the crystals become factors which affect the activity, selectivity and life of the catalysts. Hence, for provision of catalysts which can fully withstand practical use, not a few factors should be controlled. For example, in an attempt to provide practical ZSM-5 catalysts, it has previously been proposed to (i) increase the particle size of the ZSM-5 crystals by optimizing the crystallizing conditions; (ii) convert the surface of the crystals into a silanol; or (iii) grow a shell of a different composition on the exterior of the crystal grains. By these prior methods, defects attributed to imperfections in surface structure can be remedied to some extent, but this does not result in ZSM-5 catalysts having various satisfactory properties.

It is an object of this invention therefore to provide a crystalline aluminosilicate which shows fully satisfactory performance as a solid catalyst.

Another object of this invention is to provide a crystalline aluminosilicate which shows particularly high activity, good selectivity and a long active lifetime.

Still another object of this invention is to provide a crystalline aluminosilicate in which each of the crystals is constituted of an integrated mass of many small but distinguishable heterogeneous portions having different silicon/aluminum atomic ratios.

Yet another object of this invention is to provide a process for producing a crystalline aluminosilicate having the aforesaid performance and structure by hydrothermally reacting a starting mixture comprising at least two colloids having different silicon/aluminum atomic ratios.

Further objects and advantages of this invention will become apparent from the following description.

In accordance with this invention, these objects and advantages are achieved by a process for producing a crystalline aluminosilicate which comprises hydrothermally reacting a starting mixture composed of a silicon compound, an aluminum compound, an alkali metal compound, a compound capable of releasing an organic cation in water, and water, characterized in that said starting mixture comprises at least two colloids having different silicon/aluminum atomic ratios, and that the hydrothermal reaction is carried out, as required, in the presence of a fluorine compound.

The characteristic feature of the process of the invention is that a starting mixture comprising at least two colloids having different silicon/aluminum atomic ratios is hydrothermally reacted.

The raw materials used in the process of the invention may be any known materials which are normally used in the synthesis of zeolites.

Examples of the silicon compound are sodium silicate, solid silica, silica gel and silica sol. Silica sol is preferred. Silica sol is readily available under the trademarks of Ludox (Du Pont), Snowtex (Nissan Chemical Co., Ltd.) and Cataloid (Shokubai Kasei Co., Ltd.), Silica gel is available, for example, under the trademark of Syloid (Fuji-Davison Company).

A water-insoluble silicon compound such as solid silica or silica gel may be used as a solution in an alkaline aqueous solution. Many commercial grades of silica sol contain about 1000 ppm of alumina. If such silica sol is to be used, the alumina content should be considered in practicing the present invention.

The aluminum compound may, for example, be sodium aluminate or freshly prepared aluminum hydroxide. The alkali metal compound may be a sodium compound. In practice, sodium hydroxide is preferred as the sodium compound. The quality of sodium hydroxide may be of usual industrial grade. It should be noted that sodium aluminate acts both as the alkali metal compound and as the aluminum compound.

A preferred example of the compound capable of releasing an organic cation in water is a quaternary organic ammonium compound of the following general formula $$R_4NX \qquad (1)$$

wherein R is a lower alkyl group, and X is one equivalent of an anion.

The compound of formula (I) may, if desired, be formed in situ in the reaction system by using a combination of a tertiary amine of the following formula $$R_3N \qquad (2)$$

wherein R is as defined in formula (1), and a compound of the following general formula $$RX \qquad (3)$$

wherein R and X are as defined.

In the above general formulae (1), (2) and (3), R is a lower alkyl group such as methyl, ethyl, n-propyl, isopropyl, n-butyl, sec-butyl and tert-butyl.

In the general formulae (1) and (3), X is a monovalent halogen atom such as chlorine, bromine and iodine, a hydroxyl group, or one equivalent of an acid group such as a sulfuric acid group.

Examples of suitable quaternary organic ammonium compounds of general formula (1) include tetraalkyl ammonium halides such as tetrapropyl ammonium bromide, tetramethyl ammonium bromide, tetraethyl ammonium bromide, tetrapropyl ammonium chloride, tetrabutyl ammonium bromide and tetrabutyl ammonium chloride; and the hydroxides and sulfates of tetraalkyl ammoniums such as tetramethyl ammonium, tetraethyl ammonium, tetrapropyl ammonium and tetrabutyl ammonium.

Examples of suitable tertiary amines of general formula (2) include trimethylamine, triethylamine, tripropylamine and tributylamine.

Specific examples of the compound of general formula (3) are methyl bromide, ethyl bromide, propyl bromide, propyl chloride, butyl bromide, butyl chloride, methyl alcohol, ethyl alcohol, dimethyl sulfate and diethyl sulfate.

From these compounds, quaternary ammonium ions of the general formula $R_4N^+$ in which R is as defined are formed. Other organic cations may also be used.

The process of this invention is practiced by hydrothermally reacting a starting mixture prepared from the aforesaid starting compounds and water. The starting mixture is prepared from at least two colloids having different silicon/aluminum atomic ratios. The colloids may be gels or sols, preferably a combination of a gel and a sol.

Where the colloid is a gel, the gel should advantageously have the following composition in mole ratio. In the following composition, the silicon atom, the aluminum atom, the compound capable of releasing an organic cation in water, and the alkali metal compound are expressed respectively as $SiO_2$, $Al_2O_3$, $R_4N^+$, and $Na^+$ (the same expression will apply hereinafter).

| More ratio | Preferred range | More preferred range | Especially preferred range |
|---|---|---|---|
| $SiO_2/Al_2O_3$ | ≧25 | 50–3,000 | 100–2,000 |
| $R_4N^+/SiO_2$ | ≧0.01 | 0.02–1.0 | 0.03–0.4 |
| $Na^+/SiO_2$ | 0.05–0.8 | 0.10–0.7 | 0.15–0.6 |
| $H_2O/SiO_2$ | ≧10 | 15–80 | 20–70 |

The $SiO_2/Al_2O_3$ ratio in the starting mixture is determined depending upon the desired final $SiO_2/Al_2O_3$ ratio in the crystalline aluminosilicate. The increase of the $R_4N^+$ mole ratio and the decrease of the $H_2O/SiO_2$ mole ratio promote gellation, and the increase of the $Na^+/SiO_2$ mole ratio hampers gellation. Usually, gelation is performed preferably at room temperature to a temperature of 100° C., especially preferably at 100° C. The gel can be prepared in about 5 minutes to 2 hours at these temperatures.

Where the colloid is a sol, the sol should advantageously have the following composition (mol ratio).

| More ratio | Preferred range | More preferred range | Especially preferred range |
|---|---|---|---|
| $SiO_2/Al_2O_3$ | ≧25 | 50–∞ | 100–∞ |
| $R_4N^+/SiO_2$ | 0–1.0 | 0–0.8 | 0–0.5 |
| $Na^+/SiO_2$ | 0–2.0 | 0–1.5 | 0–1.4 |
| $H_2O/SiO_2$ | ≧10 | 10–500 | 20–400 |

The aforesaid commercially available silica sols may be used as sols having the above composition. The sol is usually prepared at ambient temperature, but if desired, heating or cooling may be carried out.

According to this invention, at least two colloids having different silicon/aluminum atomic ratios are preferably prepared by so-called "laminar flow mixing" or "streamline flow mixing" by which shearing is minimized.

Preferably, these at least two colloids are mixed so as to give a starting mixture having the following composition (mole ratio).

| Mole ratio | Preferred range | More preferred range | Especially preferred range |
|---|---|---|---|
| $SiO_2/Al_2O_3$ | ≧25 | 50–4,000 | 100–2,000 |
| $R_4N^+/SiO_2$ | ≧0.01 | 0.02–0.1 | 0.03–0.3 |
| $Na^+/SiO_2$ | 0.05–0.8 | 0.10–0.7 | 0.15–0.6 |
| $H_2O/SiO_2$ | ≧10 | 15–80 | 30–70 |

Furthermore, these colloids are mixed preferably in such a manner that the weight of one colloid in the starting mixture, calculated as $SiO_2$, is 0.1 to 20 times, particularly 3 to 10 times, that of at least one other colloid in the mixture. Accordingly, especially preferably, the starting material is prepared from at least one gel and at least one sol by mixing them such that the weight of at least one gel, calculated as $SiO_2$, is 0.1 to 20 times, particularly 3 to 10 times, that of at least one sol.

In order to prepare a crystalline aluminosilicate suitable as a catalyst, it is preferred to mix silica-alumina gel and silica sol and crystallize the mixture, or to mix silica gel and silica alumina sol and crystallize the mixture.

The adjustment of the quantitative ratios of the starting compounds in the starting mixture to the above ranges is important for performing sufficient crystallization by hydrothermal reaction thereby forming the desired crystals.

Surprisingly, it has been found in accordance with this invention that even if the amount of the quaternary ammonium compound is as small as described above, crystallization is not hampered but proceeds normally. This phenomenon is presumably because the quaternary ammonium compound is absorbed by the gel prepared in advance, and therefore, the subsequent crystallization proceeds around the gel.

The hydrothermal reaction in accordance with the process of this invention is carried out at a temperature of about 100° C. to about 200° C., preferably about 130° C. to about 170° C. Preferably, the hydrothermal reaction is carried out in a closed system under autogenous pressure.

The hydrothermal reaction time for crystallization varies depending upon the reaction temperature, the quantitative ratios of the compounds in the starting mixture, etc. Usually, it is about 4 to about 150 hours. For example, when the reaction temperature is 150° C., the hydrothermal reaction is usually carried out for 20 to 100 hours depending upon the starting mixture used, etc.

The hydrothermal reaction in accordance with the process of this invention may also be carried out in the presence of a fluorine compound. Investigations of the present inventors have shown that the presence of a fluorine ion in neutrality or alkalinity brings about the advantage of promoting gellation and growing crystals to a larger size.

Fluorine compounds which act as a fluorine ion source include, for example, compounds which dissociate in water to release a fluorine ion, such as sodium fluoride and ammonium fluoride; and compounds which undergo hydrolysis in water to release a fluorine ion, such as silicon fluoride, boron fluoride, and sulfur flouride. The compounds which dissociate in water to release a fluorine ion, especially sodium fluoride and ammonium fluoride, are preferred.

The fluorine compound may be caused to be present during preparation of the respective colloids, or during preparation of the starting mixture by mixing two or more colloids.

The amount of the fluorine compound used is suitably at least 0.1 mole, preferably 0.1 to 1.0 moles, especially preferably 0.2 to 0.8 mole, per mole of $SiO_2$ in the starting mixture.

Catalysts prepared from the crystalline aluminosilicates produced by the process of this invention have high selectivity and a longer active lifetime than ordinary homogenous ZSM-5 zeolites.

According to the process of this invention, a heterogeneous crystalline aluminosilicate in which the crystalline aluminosilicate portions and the crystalline silicate portions are distributed, for example, in a mosaic pattern can also be produced.

The crystalline aluminosilicates obtained by the process of this invention can be used suitably as catalysts for the isomerization, disproportionation or alkylation of hydrocarbons and the dehydration of oxygen-containing compounds. More specifically, these aluminosilicates can be used in the isomerization of xylenes, the methylation of toluene, the synthesis of olefins from methanol, and the synthesis of paraffins and aromatic compounds.

For use as catalysts, the crystalline aluminosilicates obtained by the process of this invention should be subjected to the following treatment. Crystalline aluminosilicates obtained by hydrothermal reaction in the absence of a fluorine ion are calcined, subjected to ion-exchange with ammonium chloride, and again calcined to convert them into "$H^+$ form". Crystalline aluminosilicates obtained by performing hydrothermal reaction in the presence of a fluorine ion are calcined, and then treated with an acid such as hydrochloric acid. As a result of the above treatment, fluorine contained in the crystalline aluminosilicates will sometimes decrease in amount or disappear.

It is not entirely clear why the crystalline aluminosilicates having a heterogeneous structure obtained by the process of this invention have excellent catalytic activity. It is presumed however that the heterogenous structure of the crystalline aluminosilicates affects heat transfer and material transfer within the crystals and the resulting effects are reflected on the catalytic properties of the aluminosilicates.

The crystalline aluminosilicates obtained by the process of this invention have a large particle size. As solid catalysts they have high activity and selectivity and a long active lifetime. They are also suitable as adsorbents.

The following examples illustrate the invention more specifically.

EXAMPLE 1

50.7 g of silica sol ($SiO_2$ content 30% by weight and $Na_2O$ content 0.33% by weight) and 4.7 g of sodium aluminate solution ($Al_2O_3$ content 1.2% by weight; $Na_2O$ content 2.2% by weight) were mixed with 37.8 g of water, and 6.8 g of tetrapropylammonium bromide was dissolved in the mixture with stirring. The solution was heated on a boiling water bath. After the lapse of about 15 minutes, this solution gelled.

Separately, 7.0 g of silica sol ($SiO_2$ content 30% by weight and $Na_2O$ content 0.33% by weight), 1.5 g of sodium hydroxide and 2.0 g of tetrapropyl ammonium bromide were mixed with 192.0 g of water to form a sol.

With slow stirring to afford "stream line flow mixing", the above gel and sol were mixed to form a starting mixture. The mixture was charged into an autoclave. The autoclave was closed, and maintained at 150° C. to perform hydrothermal reaction for 60 hours. After the lapse of a predetermined period of time, the crystals were withdrawn, washed and dried at 110° C. for 5 hours to obtain 19.6 g of crystals. The crystals had an average particle size of about $9\mu$ (microns)$\times 7\mu$ and showed the X-ray diffraction pattern given in FIG. 1.

The compositions in mole ratio of the gel, the sol and the starting mixture are shown in Table 1.

EXAMPLE 2

71.2 g of silica sol ($SiO_2$ content 30% by weight and $Na_2O$ content 0.33% by weight), 0.43 g of sodium aluminate ($Al_2O_3$ content 34.9% by weight; $Na_2O$ content 33.3% by weight), 1.9 g of sodium hydroxide and 24.6 g of tetrapropyl ammonium bromide were mixed with 348.2 g of water, and 4.3 g of ammonium fluoride was further added. The mixture was allowed to stand at room temperature for about 10 hours to form a gel.

Separately, 73.3 g of silica sol ($SiO_2$ content 30% by weight and $Na_2O$ content 0.33% by weight), 2.2 g of sodium hydroxide and 25.4 g of tetrapropyl ammonium bromide were mixed with 358.6 g of water to prepare a sol.

Figure 2:
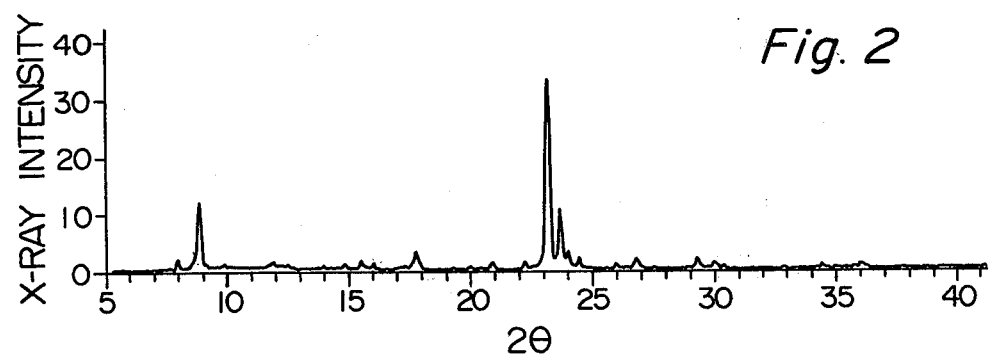

From the resulting gel and sol, 45.0 g of crystals were obtained by operating in the same way as in Example 1. The crystals had an average particle size of about $20\mu \times 5\mu$ and showed the X-ray diffraction pattern given in FIG. 2

The compositions in mole ratio of the gel, the sol and the starting mixture are shown in Table 1.

EXAMPLES 3 AND 4

Hydrothermal reaction was carried out in the same way as in Example 1 or 2 except that the compositions in mole ratio of the gel and the sol were changed as shown in Table 1. Specifically, Example 3 was operated in the same way as in Example 1, and Example 4, in the same way as in Example 2.

Figure 3:
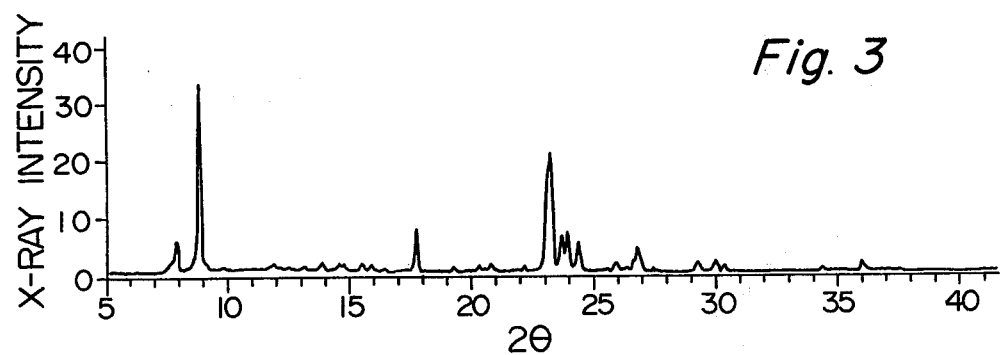

In Example 3, 30.2 g of crystalline aluminosilicate having an average particle size of about $14\mu \times 13\mu$ and showing the X-ray diffraction pattern given in FIG. 3 was obtained.

Figure 4:
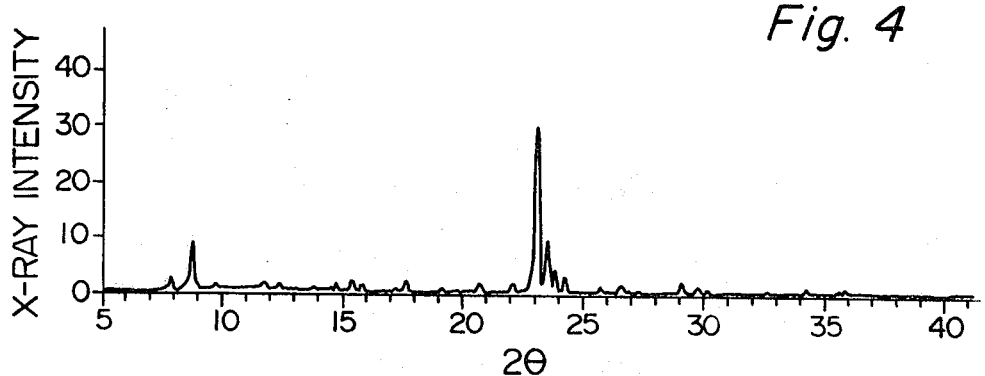

In Example 4, 33.5 g of crystalline aluminosilicate having an average particle size of about $56\mu \times 9\mu$ and showing the X-ray diffraction pattern given in FIG. 4 was obtained.

TABLE 1

| Example | | 1 | 2 | 3 | 4 |
|---|---|---|---|---|---|
| Composition of the gel (mole ratio) | $SiO_2/Al_2O_3$ | 460 | 250 | 300 | 480 |
| | $R_4N^+/SiO_2$ | 0.10 | 0.25 | 0.10 | 0.25 |
| | $Na^+/SiO_2$ | 0.03 | 0.16 | 0.03 | 0.16 |
| | $H_2O/SiO_2$ | 19.8 | 60.2 | 19.8 | 60.6 |
| | $F/SiO_2$ | 0 | 0.32 | 0 | 0.32 |
| Composition of the sol | $SiO_2/Al_2O_3$ | ∞ | ∞ | 580 | ∞ |
| | $R_4N^+/SiO_2$ | 0.20 | 0.25 | 0 | 0.25 |

TABLE 1-continued

| Example | | 1 | 2 | 3 | 4 |
|---|---|---|---|---|---|
| (mole ratio) | $Na^+/SiO_2$ | 1.37 | 0.16 | 0.43 | 0.16 |
| | $H_2O/SiO_2$ | 340 | 60.2 | 98.8 | 60.0 |
| | $F/SiO_2$ | 0 | 0 | 0 | 0.32 |
| Composition of the starting mixture (mole ratio) | $SiO_2/Al_2O_3$ | 530 | 500 | 440 | 980 |
| | $R_4N^+/SiO_2$ | 0.11 | 0.25 | 0.05 | 0.25 |
| | $Na^+/SiO_2$ | 0.16 | 0.16 | 0.23 | 0.16 |
| | $H_2O/SiO_2$ | 52.3 | 60.2 | 59.3 | 60.3 |
| | $F/SiO_2$ | 0 | 0.16 | 0 | 0.32 |

COMPARATIVE EXAMPLE 1

Figure 5:
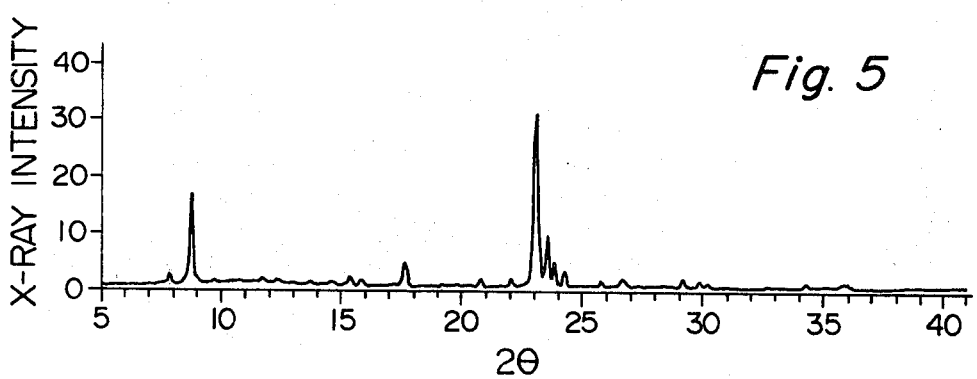

The same gel as used in Example 2 was hydrothermally reacted alone to form crystals. The resulting crystals had an average particle size of about $43\mu \times 8\mu$, and showed the X-ray diffraction pattern given in FIG. 5.

COMPARATIVE EXAMPLE 2

Figure 6:
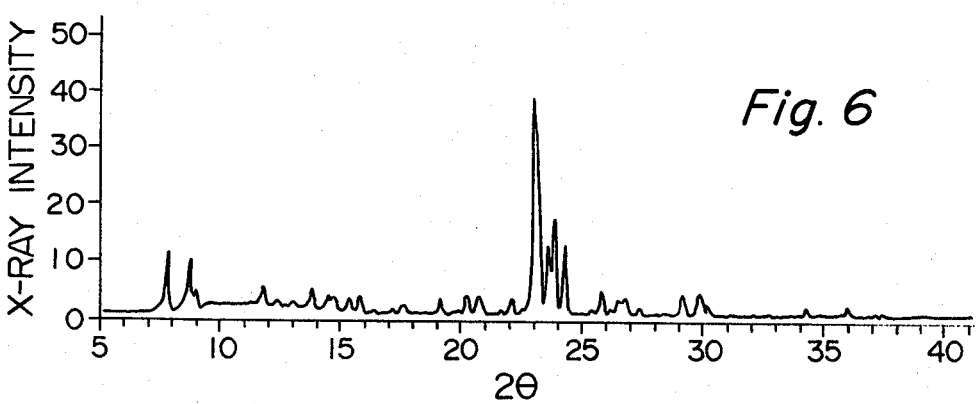

The same sol as used in Example 2 was hydrothermally reacted alone to form crystals. The resulting crystals had an average particle size of about $12\mu \times 6\mu$ and showed the X-ray diffraction pattern given in FIG. 6.

COMPARATIVE EXAMPLE 3

The same gel as used in Example 3 was hydrothermally reacted alone. No crystal was formed.

COMPARATIVE EXAMPLE 4

The same sol as used in Example 3 was hydrothermally reacted alone to form crystals. The resulting crystals were mordenite crystals.

REFERENTIAL EXAMPLE (1) The crystalline aluminosilicate obtained in Example 2 was calcined in the air at 550° C. for 5 hours, and then contacted with an 18% by weight aqueous solution of hydrochloric acid at 90° C. for 5 hours. The solid was separated by filtration, and washed with water until no chlorine ion was detected in the washing. It was finally dried at 110° C. for 10 hours.

Silica sol and titanium dioxide powder were added to the dried crystals, and they were well kneaded. The mixture was molded into tablets by using a porous plate (1.5 mm $\phi \times 2$ mm H). After drying, the tablets were taken out from the porous plate, and calcined in the air at 550° C. for 5 hours to form a catalyst. The resulting catalyst contained 67% by weight of crystalline aluminosilicate, 13% by weight of silica and 20% by weight of titanium dioxide.

4.4 ml of the aforesaid catalyst was filled in a reaction tube having a sectional area of 7.3 cm$^2$ to a height of 0.6 cm. The catalyst bed was maintained at 335° C., and methanol was passed through the catalyst bed at a feed rate (LHSV) of 1.2 hr$^{-1}$ under atmospheric pressure without using a diluent.

The amount of methanol supplied was 1.6 g per m$^2$ of crosssectional area per second, and the linear velocity of the methanol vapour was 0.11 cm/sec. The results of the reaction are shown in Table 2.

(2) 0.28 g of sodium aluminate ($Al_2O_3$ content 34.9% by weight; $Na_2O$ content 33.3% by weight), 2.9 g of sodium hydroxide and 2.8 g of ammonium fluoride were dissolved in 471.3 g of water. Then, 31.7 g of tetrapropyl ammonium bromide prepared in advance was added to form a uniform aqueous solution. Furthermore, 71.2 g of silica sol ($SiO_2$ content 40% by weight) was added to the aqueous solution, and the mixture was put in a mixer and treated at a rotating speed of 10,000 rpm (the linear velocity of the blade tip 45 m/sec.) at room temperature for 3 minutes while imparting a shearing force. The composition of this starting mixture was the same (see Table 1) as that of the starting mixture used in Example 2.

The starting mixture was charged into an autoclave, and hydrothermally reacted in the same way as in Example 1 to form crystals. In the same way as set forth in (1) above, the crystals were calcined and treated with an acid, and silica sol and titanium dioxide powder were added, after which the mixture was molded, calcined, and used as a catalyst. The results are also shown in Table 2 in the parentheses.

TABLE 2

| | 26 hours after the initiation of the reaction | 126 hours after the initiation of the reaction |
|---|---|---|
| Methanol conversion (%) | 96.5 (94.0) | 87.9 (83.1) |
| Hydrocarbon selectivity (wt. %) | 42.6 (42.2) | 34.6 (33.2) |
| Dimethyl ether selectivity (wt. %) | 1.9 (2.6) | 15.1 (19.7) |
| Water selectivity (wt. %) | 55.5 (55.2) | 50.3 (47.1) |
| Proportions (wt. %) of hydrocarbons | | |
| Ethylene | 28.7 (25.2) | 34.5 (31.1) |
| Propylene | 12.6 (14.3) | 20.4 (21.5) |
| Butene | 10.3 (11.5) | 9.7 (13.4) |
| Methane | 0.4 (0.4) | 0.7 (0.5) |
| Ethane | 0.1 (0.1) | 0.1 (0.1) |
| Propane | 3.4 (2.9) | 2.0 (2.3) |
| i-Butane | 4.3 (3.2) | 2.5 (2.6) |
| n-Butane | 1.2 (1.0) | 0.6 (0.7) |
| i-Pentane | 6.2 (5.4) | 3.5 (3.0) |
| Other hydrocarbons | 32.8 (36.0) | 25.9 (24.8) |

What we claim is:

1. A process for producing a crystalline aluminosilicate which comprises hydrothermally reacting a starting mixture composed of a silicon compound, an aluminum compound, an alkali metal compound, a compound capable of releasing an organic cation in water, and water to form a crystalline aluminosilicate in which each of the crystals is constituted by an integrated mass of many small but distinguishable heterogeneous portions having different silicon/aluminum atomic ratios, wherein said starting mixture comprises at least two types of colloids having different silicon/aluminum atomic ratios, said two types of colloids being two members selected from the group consisting of a gel having the following composition in mole ratio:

$SiO_2/Al_2O_3$: $\geq 25$
Organic cation/$SiO_2$: $\geq 0.01$
Alkali metal cation/$SiO_2$: 0.05–0.8
$H_2O/SiO_2$: $\geq 10$ and a sol having the following composition in mole ratio:

$SiO_2/Al_2O_3$: $\geq 25$
Organic cation/$SiO_2$: 0–1.0
Alkali metal cation/$SiO_2$: 0–2.0
$H_2O/SiO_2$: $\geq 10$.

2. The process of claim 1 wherein said two types of colloids comprises both said gel and said sol.

3. The process of claim 1 wherein said starting mixture has the following composition in mole ratio:

$SiO_2/Al_2O_3$: $\geq 25$
Organic cation/$SiO_2$: $\geq 0.01$
Alkali metal cation/$SiO_2$: 0.05–0.8
$H_2O/SiO_2$: $\geq 10$.

4. The process of any one of claims 1 to 3 wherein the organic cation is a quaternary organic ammonium ion.

5. The process of any one of claims 1 to 3 wherein the alkali metal cation is a sodium ion.

6. The process of claim 1 wherein one colloid in said starting mixture is present in a weight, calculated as $SiO_2$, 0.1 to 20 times the weight of other colloid in said mixture.

7. The process of any one of claims 1 to 3 wherein said starting mixture is composed of said gel and sol, and the weight of said gel calculated as $SiO_2$ is 0.1 to 20 times the weight of said sol.

8. The process of claim 1 wherein said starting mixture further contains a fluorine compound, which promotes gellation and crystal growth, in an amount of at least 0.1 mole per mole of the starting mixture calculated as $SiO_2$.

9. The process of claim 8 wherein said fluorine compound is a compound which dissociates in water to release a fluorine ion.

10. The process of claim 8 or 9 wherein said fluorine compound is sodium fluoride or ammonium fluoride.

11. The process of claim 8 wherein said fluorine compound is a compound which undergoes hydrolysis in water to release a fluorine ion.

12. The process of claim 8 or 11 wherein said fluorine compound is silicon fluoride, boron fluoride or sulfur fluoride.

13. The process of claim 1 wherein the hydrothermal reaction is carried out at a temperature of about 100° C. to about 200° C.

14. The process of claim 1 wherein said starting mixture is prepared by mixing said at least two types of colloids having different silicon/aluminum ratios by laminar flow mixing wherein shearing is minimized.

* * * * *